Figure 1:
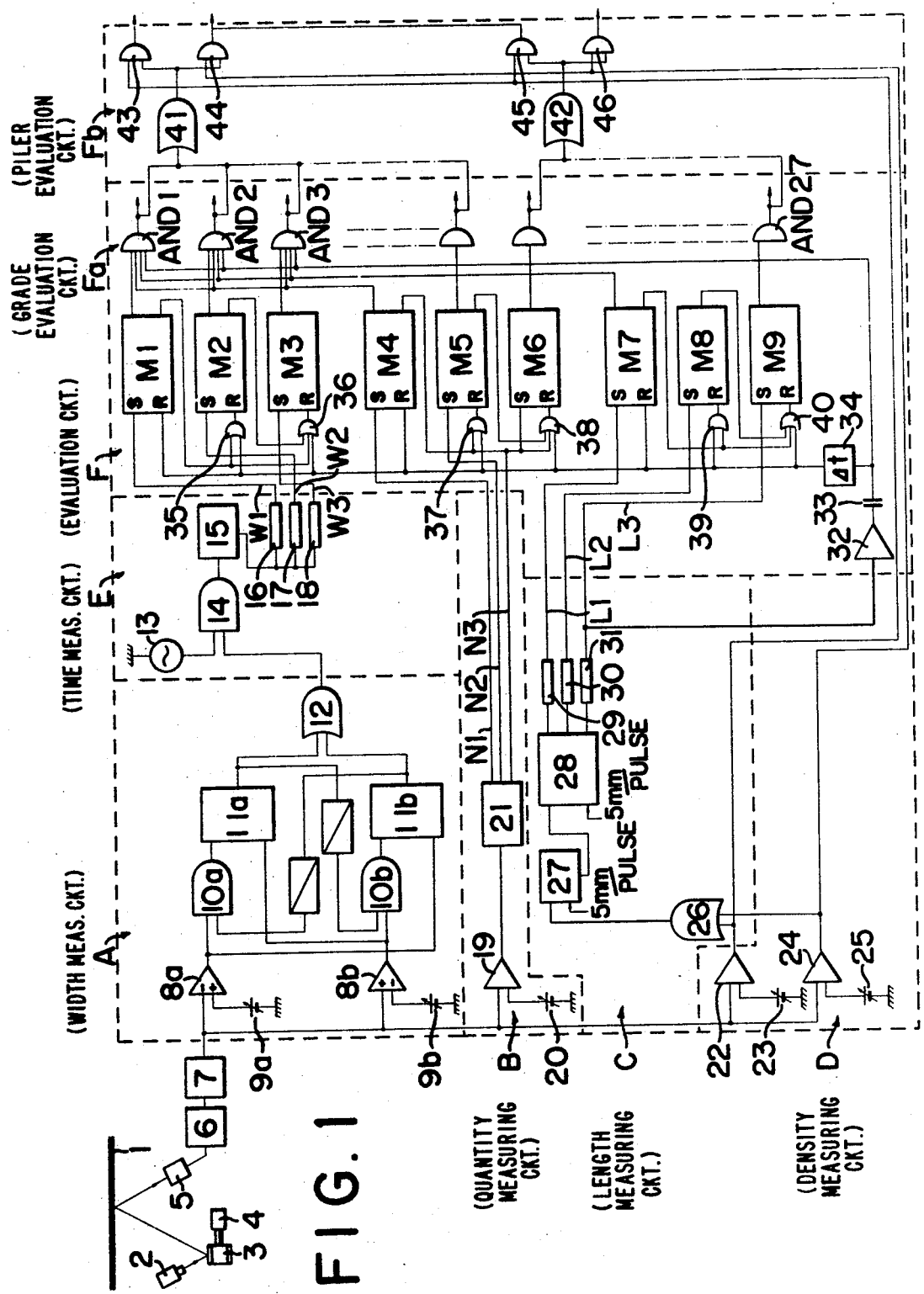

United States Patent [19]

Akutsu et al.

[11] 4,110,048
[45] Aug. 29, 1978

[54] METHOD OF AND AN APPARATUS FOR INSPECTING A TRAVELING SHEET MATERIAL

[75] Inventors: Shoji Akutsu; Yasumasa Watanabe; Yasuhiko Mashino, all of Chiba; Tomohiro Chaki; Masakazu Fujita, both of Tokyo, all of Japan

[73] Assignees: Kawasaki Steel Corporation; Toei Denshi Kogyo Kabushiki Kaisha, Tokyo, both of Japan

[21] Appl. No.: 705,826

[22] Filed: Jul. 16, 1976

Related U.S. Application Data

[63] Continuation of Ser. No. 521,159, Nov. 5, 1974, abandoned.

[51] Int. Cl.$^2$ ............................................. G01N 21/16
[52] U.S. Cl. ..................................... 356/200; 250/563
[58] Field of Search ......................... 356/199, 200, 73; 250/563, 572

[56] References Cited

U.S. PATENT DOCUMENTS

| 3,096,443 | 7/1963 | Laycak | 356/200 |
| 3,515,488 | 6/1970 | Houser | 356/200 |
| 3,779,649 | 12/1973 | Bertoya | 356/200 |
| 3,781,117 | 12/1973 | Laycak et al. | 356/200 |
| 3,781,531 | 12/1973 | Baker | 250/572 |
| 3,833,816 | 9/1974 | Emura et al. | 356/199 |

Primary Examiner—Vincent P. McGraw
Attorney, Agent, or Firm—Henry R. Lerner

[57] ABSTRACT

A method of and an apparatus for inspecting a traveling sheet material, in which the ability to detect a defect is made as close to the identifying ability of man's visual inspection as possible, the detected defect is converted into an electrical signal and separated into four factors of width, quantity, depth or density, and length to make the sorting process most economical, the factors are discriminated to be of high, medium or low class, respectively, and the discriminated defect factors are synthetically judged through a decision circuit according to a defect pattern.

15 Claims, 7 Drawing Figures

METHOD OF AND AN APPARATUS FOR INSPECTING A TRAVELING SHEET MATERIAL

This is a continuation of application Ser. No. 521,159, filed Nov. 5, 1974, and now abandoned.

The present invention relates to a method of and an apparatus for inspecting a traveling ribbon or sheet material such as sheet steel, non-ferrous metal plate, paper, film or the like, more particularly, to a method and an apparatus to classify a plurality of factors of a defect in such sheet material with respect to the width, quantity, depth or density, and length of the defect, and to determine the degree of the defect by judging it synthetically in the light of the predetermined degrees of defect.

Conventionally, a visual inspection has been utilized for inspecting and sorting defects on the surface of a traveling sheet material such as sheet steel. The visual inspection method, however, depends on the capability, experience and skillfulness of the inspector, posing various problems and resulting in nonuniformity of inspection accuracy and restriction of industrial production capacity. It is said, for example, that if a visual inspector continuously inspects a shearing process line in excess of three hours, the inspection accuracy quickly decreases and inspection uniformity deteriorates. The cause is considered to be the inspecting ability of the inspector much relying on his experience and intuition, which becomes unable to follow the change in surface quality of the material to be inspected, although it is somewhat different according to the individuality of the inspector.

To eliminate the above inconvenience as well as to improve the inspection accuracy, to save manpower, to automate the inspection process and to increase the industrial capacity, some means for automatically inspecting the surface defect in traveling sheet material have been developed and put in practical use. However, the inspecting of the surface defect in sheet steel or the like requires synthetical ability of discrimination, and no automatic inspection method (and equipment) functionally comparable to the visual ability and judgment based thereon of human being has yet been developed.

The visual inspection and judgment based thereon can be replaced by an artificial means if the expected judgment results of visual inspection are made into a numeric scale and the results detected by a machine are made coincident with the scale. For this purpose, it is very important how to place all defects on a single line at all times. If a certain defect is over-detected, the production yield decreases; if it is under-detected, the product of inferior quality is made into merchandise.

The present invention solves these problems by separating one kind of defect into a plurality of numerical factors and judging a detected defect in the light of these factors as combined.

A color defect of sheet steel much affects the attenuation of light quantity, and this defect is easy to detect and is over-detected sometimes although the defect hardly causes a problem in practical use of the material. A scratch, pinhole or other minute defect on an aventurine surface of surface-treated sheet steel has no great effect on the attenuation of light quantity and is difficult to detect although the defect must be inspected very severely as it may pose a serious problem in practical use of the material. Use of conventional simple detectors in inspecting these various defects is accompanied with a large error, and therefore requires the judgment of their operator in order to assist the performance of the detectors.

An object of the present invention is to provide an automatic inspection method and apparatus comparable to the visual inspection by human being in the discriminating ability as well as preferable for automatic on-line detection and sorting of the surface detects in traveling sheet material.

According to the present invention, the ability to detect a surface defect is made as close to the identifying ability of man's visual inspection as possible, the defect is converted into an electrical signal and analyzed into the four factors of width, quantity, depth or density, and length. To make the sorting process most economical, the factors are discriminated to be of high, medium or low class, respectively, and the discriminated defect factors are synthetically judged through a decision circuit according to a defect pattern.

By preparing the defect pattern beforehand, the present invention provides accurate detection regarding the aforementioned color defect which is apt to be over-detected as well as the serious defects such as scratch and pinhole which tend to be under-detected.

Figure 2:
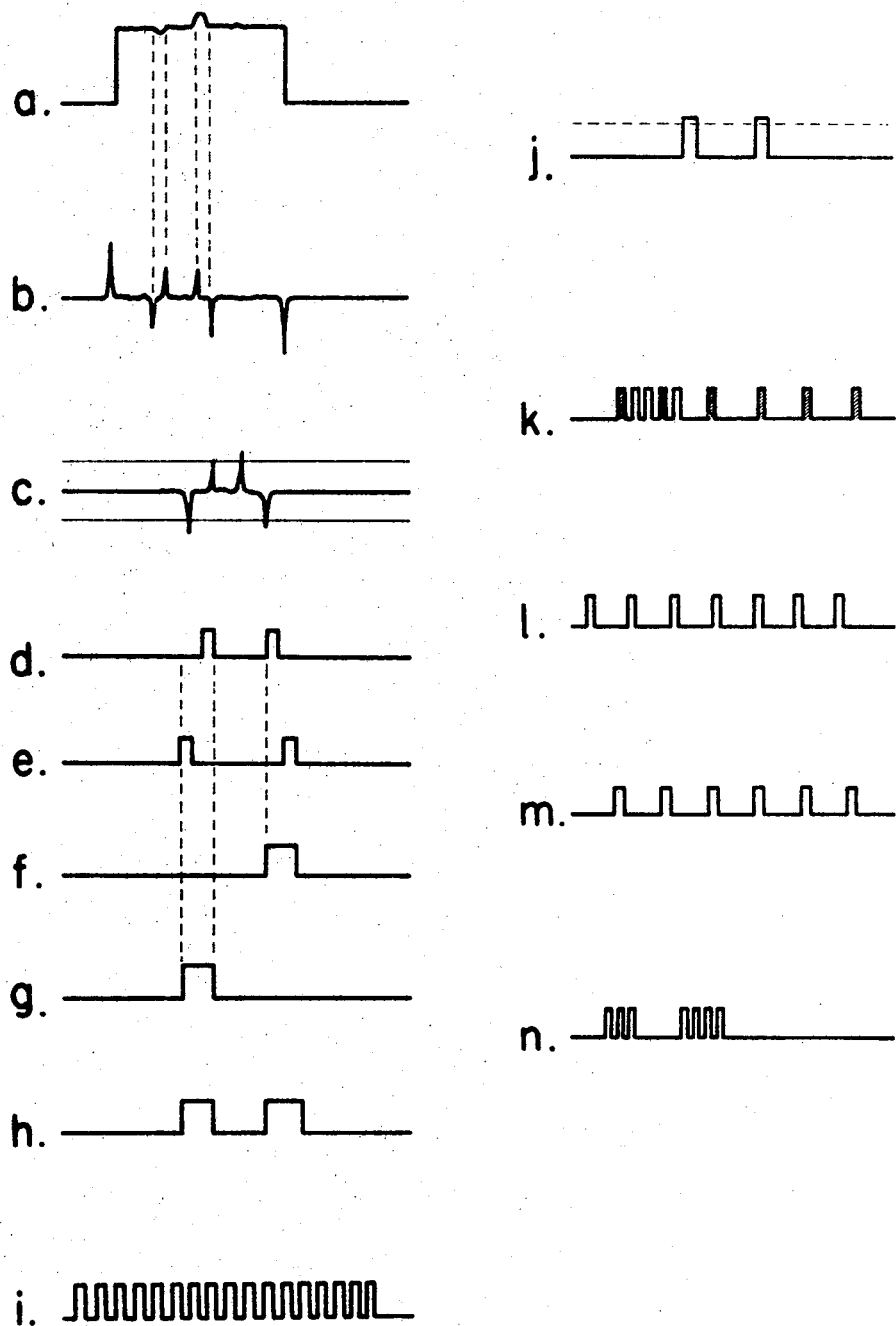

The invention will now be described, by way of example, with reference to the accompanying drawings, in which:

FIG. 1 is a block diagram showing an embodiment according to the present invention, FIG. 2 is a waveform diagram of the signals in connection with the embodiment shown in FIG. 1, FIGS. 3 to 7 are waveform diagrams for the purpose of explaining the operations of the embodiment.

Referring now to FIG. 1, a traveling sheet material 1 such as cold-rolled sheet steel is fed forwardly, in the predetermined direction, at substantially constant speed. To one side of the sheet material 1 a light source 2 is positioned to direct a light beam on to a mirror member 3 which has a plurality of identical mirrored faces and is driven to rotate at constant speed by an electric motor 4, the light beam impinging on the faces in succession as the member 3 rotates in the predetermined direction. By this arrangement, the light beam reflected from the member 3 makes successive scans across the sheet material 1. The light paths are shown in FIG. 1 by solid lines. A photodetector means 5 is arranged to receive the beam reflected by the surface of the sheet material 1. If the material to be inspected is transparent, the photodetector 5 may be arranged to receive the beam transmitted through the sheet material 1. If there is any defect in the surface of the sheet material 1, light from the surface will be scattered by the defect when it is struck by the beam. Thus, the light beam may be varied in light quantity at the time of reflection by the surface of the sheet material 1. The reflected light beam from the surface of the sheet material 1 is received by the photodetector 5, in which the variation in the light quantity of the received light beam is converted into an electric signal as defect signal. The defect signal is properly amplified by an amplifier 6. The amplified signal is then fed into a blanking circuit 7, in which the signal is differentiated and amplified and both edges are erased.

A circuit arrangement shown in FIG. 1 comprises a defect width measuring circuit A, a defect quantity measuring circuit B, a defect length measuring circuit C, a defect depth or density measuring circuit D and a time measuring circuit E. The class of defect factor determined by each of the circuits A, B, C and D will be fed into an evaluation circuit F for synthetic judgment.

Regarding the defect width measuring circuit A, the input from the blanking circuit 7 has a dark defect signal I or bright defect signal II, whose waveform is as shown in FIG. 3a. With a decay pulse a1 as in FIG. 3a due to the dark defect signal, a pulse c1 as in FIG. 3c is produced through a differential amplifier 8a having a reference voltage source 9a, and is supplied to an inhibit circuit 10a and flip-flop 11b, the output of which is connected to the inhibit input of the inhibit circuit 10a. At the time the aforementioned pulse c1 is fed in, however, no inhibit is applied; therefore, a flip-flop 11a is set. Next, with the rise pulse a2 due to the dark defect signal, a pulse b1 as in FIG. 3b is produced through a differential amplifier 8b having a reference voltage source 9b, and is supplied to an inhibit circuit 10b and simultaneously fed into the reset side of filip-flop 11a, at which time the flip-flop 11a is reset. Since the inhibit circuit 10b meets the inhibit condition during the set period of the flip-flop 11a, the flip-flop 11b is not set.

For the bright defect signal, the flip-flop 11b is set with the pulse b2 as in FIG. 3b due to a pulse a3 as in FIG. 3a, and is reset with the pulse c2 as in FIG. 3c due to a pulse a4 as in FIG. 3a. These outputs of the flip-flops 11a and 11b are fed to an OR circuit 12.

Figure 3:
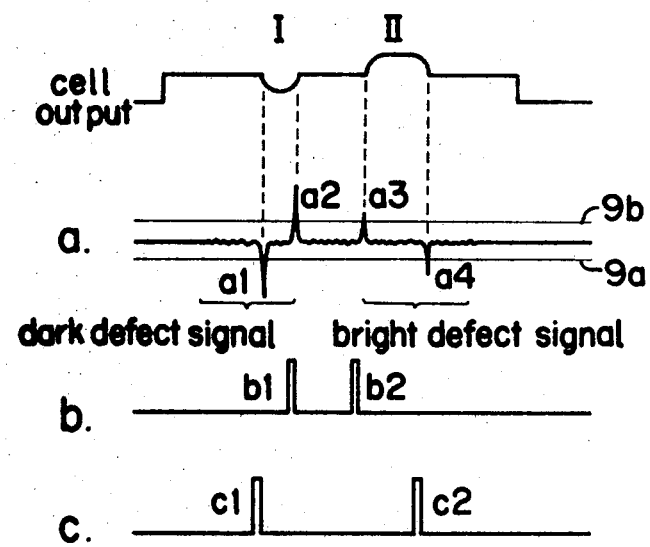
Figure 4:
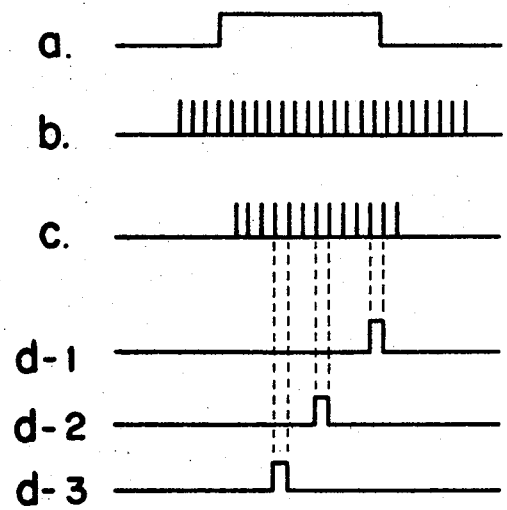

Output of the OR circuit 12 is converted into one of three width classes, for example, large width W1, medium width W2 and small width W3, by a time measuring circuit E which comprises, for example, a preset counter, monostable multivibrator or other means. With an example of the time measuring circuit E being a preset counter, input from an oscillator 13 and output signal of the aforementioned OR circuit 12 are fed into an AND circuit 14, the output of which is supplied to a counter 15. After the counting, the signal is identified to be large width W1, medium width W2 or small width W3 by using counter set-value output circuits 16, 17 and 18. Output waveforms in the above process are as shown in FIG. 4. FIG. 4a shows the output waveform of the OR circuit 12, FIG. 4b shows the output waveform of the oscillator 13, and FIG. 4c shows the output waveform of the AND circuit 14. Waveforms as in FIGS. 4d-1, 4d-2 or 4d-3 for large width W1, medium width W2 or small width W3 are obtained as a result. With an example of the time measuring circuit E being composed of monostable multivibrators, the output of the OR circuit 12 is supplied to large- and medium-width set monostable multivibrators and to medium- and small-width set monostable multivibrators, and their respective outputs are supplied (together with the direct output of the OR circuit 12) to an AND circuit for discrimination of the signal.

Figure 5:
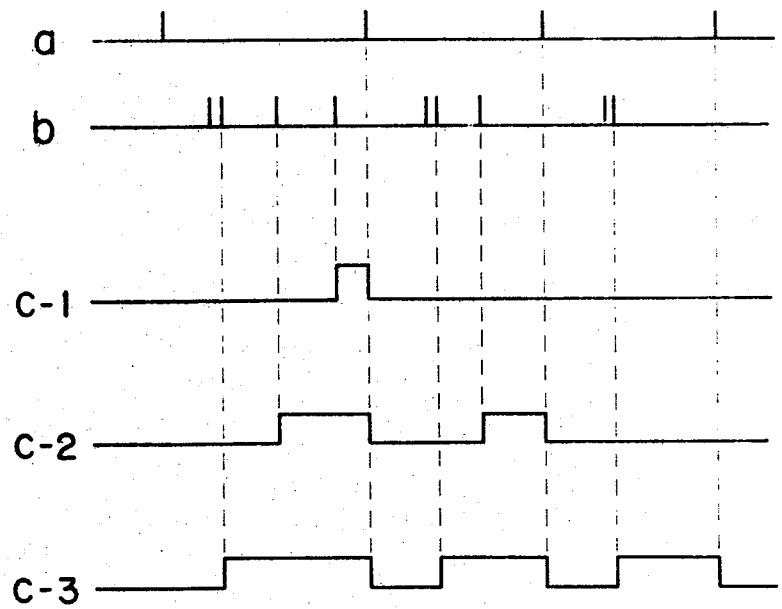

Regarding the defect quantity measuring circuit B, a differential amplifier 19 is supplied with the output of the blanking circuit 7. The output signals of the amplifier 19 which are in excess of a reference voltage 20 are counted by a counter 21, and then identified to be a large quantity N1, medium quantity N2 or small quantity N3 by using counter set-value output circuits. The counter 21 is reset by the edge blanking pulse at the rear. The waveforms in the above process are as shown in FIG. 5. FIG. 5a shows the waveform of reset pulse, FIG. 5b shows the output waveform of the blanking circuit 7, FIG. 5c-1 shows the waveform of large quantity N1 through the counter set-value output circuit, FIG. 5c-2 shows the waveform of medium quantity N2, and FIG. 5c-3 shows the waveform of small quantity N3. In the case of FIG. 5, N1 is set to 4, N2 is set to 3 and N3 is set to 2.

Regarding the defect depth or density measuring circuit D, the output of the blanking circuit 7 is fed into differential amplifiers 22 and 24, and their respective signals which are in excess of reference levels 23 and 25, respectively, are supplied to the evaluation circuit F and simultaneously to the defect length measuring circuit C. In the above process, the output of the differential amplifier 22 or 24, for which the reference voltage 23 or 25 is higher than the other in peak output value, is given as a greater depth or density output. Further, the outputs of the differential amplifiers 22 and 24 are passed through an OR circuit 26 to set a flip-flop 27, which will be reset with a line synchronizing pulse (5 mm/pulse) thereafter. The flip-flop 27 will not be reset if it receives the signal from the OR circuit 26 before the occurrence of the line synchronizing pulse. If there are two or more line synchronizing pulses in succession, it is judged that there is no defect, and the flip-flop 27 is reset. Thus, a counter 28 is arranged to be set and reset by the flip-flop 27, counts line synchronizing pulses, and sends the counted output to the counter set-value output circuits 29, 30 and 31, respectively, for sequential output beginning with what reaches the counter set-value.

Figure 6:
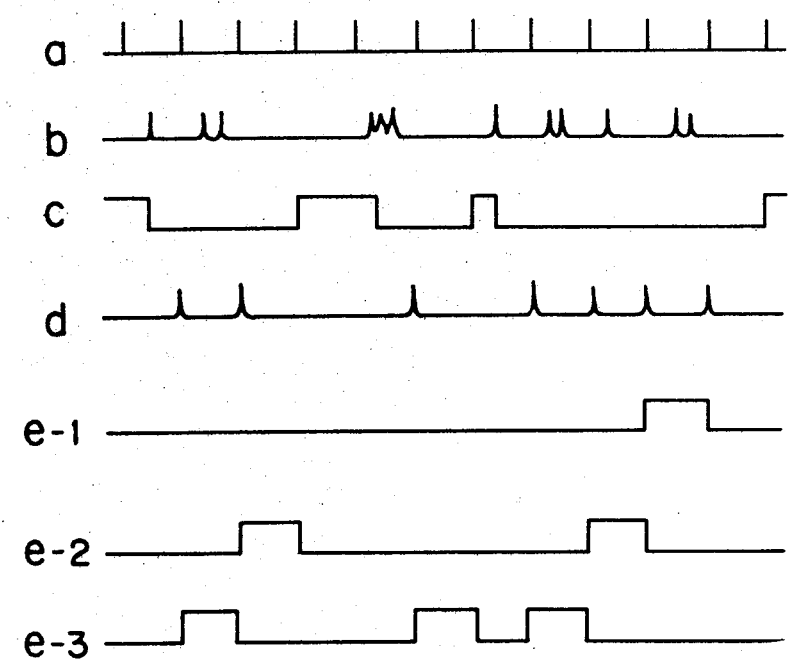

FIG. 6 shows the waveforms during the process, in which a is the waveform of the line synchronizing signal (5 mm/pulse), b is the output waveform of the OR circuit 26, c is the output waveform of the flip-flop 27, d is the input waveform of the counter 28, and e-1, e-2 and e-3 are the waveforms of the counter set-value output circuits 29, 30 and 31 which identify large length L1, medium length L2 and small length L3, respectively.

How the circuits shown in FIG. 1 operate will be described by referring to the waveforms shown in FIG. 2.

The quantity of the light incident upon a traveling sheet material 1 is changed at the place of a defect as shown with the output signal waveform of the photodetector 5 which is shown in FIG. 2a. The output signal of the photodetector 5 is amplified by the amplifier 6, and is differentiated by the blanking circuit 7 into a waveform as shown in FIG. 2b. From the differentiated waveform, both edge portions due to the photodetector 5 are erased by the effect of edge blanking for making the waveform into a one as shown in FIG. 2c.

The differential amplifier 8a in the circuit A issues a rectangular wave with the defect signal the level of which is higher than a certain level 9a, the waveform of the rectangular signal being as shown in FIG. 2d. Similarly, a rectangular wave as shown in FIG. 2e is issued by the differential amplifier 8b in the circuit A for a defect signal of negative polarity the level of which is lower than a certain level 9b. For obtaining the signal representing the width of the defect, output signals (FIGS. 2d and 2e) of the differential amplifiers 8a and 8b, are turned on and off to be waveforms as shown in FIGS. 2f and 2g, respectively, and these signals are composed into a rectangular wave signal as shown in FIG. 2h. Clock pulses as in FIG. 2i are issued separately at a constant repetition rate, and coincidence of the rectangular signal with the clock pulses is taken to produce a defect width signal as shown in FIG. 2n. For example, if there are four clock pulses of 100 $\mu$/pulse, the defect width is 400 $\mu$. For detecting the number of defects, the differential amplifier 19 is used for feeding the counter 21 with only those defect signals the level of which is higher than a reference level 20. The counter 21 the output signal of which has a waveform as shown in FIG. 2j is reset with a rear edge blanking pulse after each scanning section is scanned.

For measuring the length of defect the outputs of the differential amplifiers 22 and 24 are fed to the OR circuit 26, the output of which has the waveform as shown in FIG. 2k, in which the shaded pulses denote a continuous defect. The pulse duration is related to the period of scanning, and one pulse is issued when there is a defect within one unit section of scanning width. In other words, there is output of one pulse for each unit section of scanning width (5 mm in the case of this example) at all times. Different from the above, a clock pulse is generated at every unit section of scanning and is fed into the counter 28. If there is no defect signal within the period of one scanning section, the flip-flop 27 is reset for resetting the counter 28. If there is a defect signal within the period of one scanning section, the flip-flop remains turned on, and counting continues. The waveforms of the counter input signals to the counter 28 is as shown in FIG. 2l and the output of counter 28 is shown in FIG. 2m. Because of 5 mm/pulse, the six pulses shown in FIG. 2m represent a defect length of 30 mm.

For measuring the depth of defect, the reference levels 23 and 25 of the differential amplifiers 22 and 24 are set to high and low levels, respectively, so that the depth of defect may be detected as a deep or shallow one, the signal of which will be supplied to the evaluation circuit F.

The evaluation circuit F consists of a defect grade evaluation circuit Fa and a piler evaluation circuit Fb. The defect grade evaluation circuit Fa comprises the nine memories M1 to M9 corresponding to the three defect width classes W1, W2 and W3 of the output from the defect width measuring circuit A, three defect quantity classes N1, N2 and N3 of the output from the defect quantity measuring circuit B, and three defect length classes L1, L2 and L3 of the output from the defect length measuring circuit C, and also comprises the 27 4-input AND circuits AND1 to AND27 the inputs to which are the outputs of the memories M1 to M9 and the defect grade output command signal produced from counter circuit 31 through the waveform shaper circuit consisting of an inverter 32 and a capacitor 33. The output of the defect grade evaluation circuit Fa which identifies one of 27 defect grades is used for printer output and also is supplied to the pile evaluation circuit 5b for pile-operating output.

The defect grade output command signal from the above-mentioned capacitor 33 is supplied through a time delay circuit 34 for resetting the aforementioned memories M1, M4 and M7. As the signals to reset the other memories, M2, M3, M5, M6, M8 and M9, outputs of their respective preceding memories M1, M2, M4, M5 and M8 are partially applied through OR circuits 35, 36, 37, 38, 39 and 40, respectively.

Figure 7:
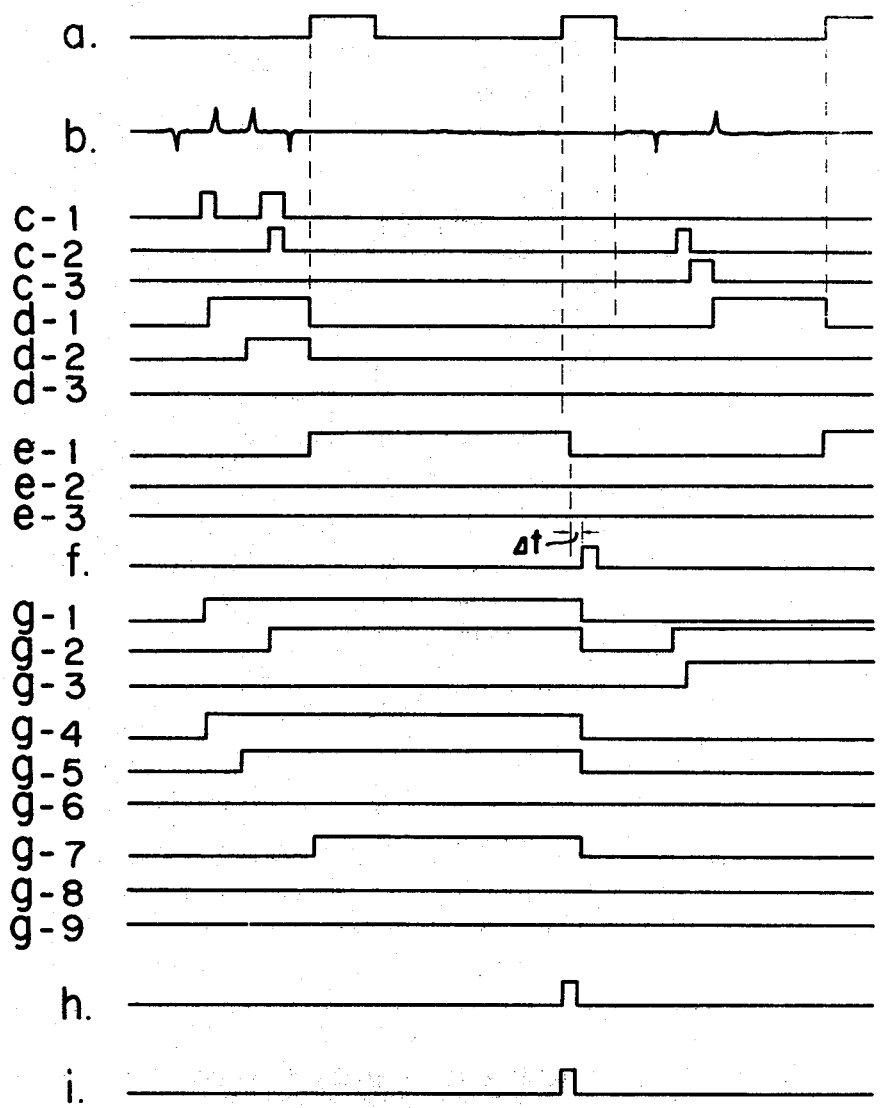

FIG. 7 shows waveforms of the signals in connection with the defect grade evaluation circuit. Waveform a is the blanking output, waveform b is the output of the blanking circuit 7, waveforms c-1, c-2 and c-3 are outputs of small defect width W3, medium defect width W2 and large defect width W1, waveforms d-1, d-2 and d-3 are outputs of small defect quantity N3, medium defect quantity N2 and large defect quantity N1, waveforms e-1, e-2 and e-3 are outputs of small defect length L3, medium defect length L2 and large defect length L1, waveform f is a memory set signal, waveforms g-1 to g-9 are outputs of the memories M3, M2, M1, M6, M5, M4, M9, M8 and M7, respectively, waveform h is a defect grade output command signal, and waveform i is the AND gate output of, for example, the AND circuit AND3 with which coincidence of the four AND inputs is attained.

The 27 grades of defect identifiable as above are grouped, from the viewpoint of practical usability of the sheet material, into those of higher degree and those of lower degree beforehand. The signals of these two degrees are fed into the two OR circuits 41 and 42, respectively, of the pile evaluation circuit Fb, and their outputs are supplied, together with the larger or smaller depth or density output from the differential amplifier 22 or 24 of the defect depth or density circuit D, to two AND gates 43 and 44, or 45 and 46 for obtaining three piler-operating output signals.

As in the foregoing, the present invention enables any defect in sheet material to be classified to one of the 27 defect grades and the found defect grade to be printed, permitting the usability of the product to be determined according to the defect grade, necessary actions to be taken in the succeeding process, the cause of the defect due to the preceding process to be examined, and the result to be utilized various other purposes, in addition to giving a piler-operating output according to the degree of defect, with which the steel sheet transported on a conveyor is sorted to be of fair quality, to be usable for less quality-sensitive purposes or to be unusable at all by means of reject gates.

The present invention achieves better results of inspection than the stationary visual inspection by human being. Also, the present invention provides a full automatic sorting means, unlike the conventional surface inspecting methods which generally convert the change in light quantity caused by a defect into electricity for detecting the defect and is therefore unable to identify the type of defect, failing to develop a full automatic sorting means.

The foregoing description of the preferred embodiments of the invention is given here by way of example only. The invention is not to be taken as limited to any of the specific features as described, but comprehends all such variations as come within the scope of the appended claims.

What is claimed is:

1. Apparatus for inspecting a traveling sheet material for determining characteristics of defects in said material, said apparatus comprising a light source and a means for scanning a beam of said light source across said traveling sheet material, photodetector means arranged to receive light reflected from said sheet material, and wave shaping means connected to said photodetector means for shaping the signal received from said photodetector means, said photodetector means receiving scattered light as said beam intersects the boundaries of a defect, said wave shaping means providing a positive pulse as said scanning light beam crosses one side boundary of said defect and providing a negative pulse as said scanning light beam completes its traversement of the defect and crosses the other side of said defect, said apparatus further comprising;

first pulse forming means connected to said wave shaping means responsive to said pulse of one polarity to generate a step pulse and responsive to the next pulse of an opposite polarity to terminate said step pulse, whereby the length of said step pulse corresponds to the width of said defect, second pulse forming means connected to said wave shaping means for generating a pulse each time a pulse of one polarity is generated by said wave shaping means, first counter means connected to count the number of pulses generated by said second pulse forming means, and means to read said count each time a scan is completed, the number counted by said first counter means equalling the number of defects sensed by said scanning light beam each time it traverses said sheet of material, and third pulse forming means connected to said wave shaping means for generating a pulse each time a pulse of one polarity is generated by said wave shaping means, a second counter, counting pulses supplied to said second counter, said counting pulses being synchronized with said scanning light, first logic circuit means connected between said third pulse forming means and said second counter for enabling said second counter to increment its count each time a counting pulse is provided and said third pulse forming means successively produces a pulse, whereby said second counter keeps counting for each scan so long as a defect is present to provide a count corresponding to the length of said defect.

2. Apparatus as set forth in claim 1, wherein said first logic circuit means resets said second counter when said third pulse forming means terminates generating successive pulses.

3. Apparatus as set forth in claim 1, comprising at least two differential amplifier means, with their inputs connected together and to said wave shaping means, each of said differential amplifiers being provided with a respective different reference voltage level, whereby the respective differential amplifier providing an output represents the depth of the defect, the pulse height of said wave shaping means having an amplitude corresponding to the depth of said defect.

4. Apparatus as set forth in claim 1, wherein said third pulse forming means comprises said at least two differential amplifiers, and an OR gate connected to receive the outputs from said at least two differential amplifiers.

5. Apparatus as set forth in claim 1, wherein said first pulse forming means comprises first means to sense when the output of said wave shaping means exceeds a predetermined positive voltage level and second means to sense when the output of said wave shaping means exceeds a predetermined negative voltage level, and second logic circuit means connected to the outputs of said first and second means to sense for generating a pulse when said first and second means to sense their respective positive and negative voltage levels.

6. Apparatus as set forth in claim 1, wherein said wave shaping means supplies a reset signal to reset said first counter each time a scan section is completed.

7. Apparatus as set forth in claim 1, wherein said first logic means comprises a flip-flop, said third pulse forming means setting said flip-flop when said pulse of one polarity is generated, said flip-flop being connected to said second counter and resetting said second counter when said flip-flop is reset, said counting pulses being supplied to said flip-flop to reset said flip-flop, said flip-flop preventing said second counter from counting when said flip-flop is in a reset state, said second counter commencing to count when two successive counting pulses are received at said second counter and said flip-flop is in said set state each time said successive counting pulses is received.

8. Apparatus as set forth in claim 1, further comprising defect width grading means connected to said first pulse forming means to grade the width of the defect, defect quantity grading means connected to said first counter to grade the quantity of said defects, and defect length grading means to grade the defect length, and first means to combine said defect width grading means, said defect quantity grading means and said defect length grading means to synthetically judge the grade of the sheet material defects.

9. Apparatus as set forth in claim 8, comprising at least two differential amplifier pressure means, with their inputs connected together and to said wave shaping means, each of said differential amplifiers being provided with a respective different reference voltage level, whereby the respective differential amplifier providing an input represents the depth of the defect, the pulse height of said wave shaping means having an amplitude corresponding to the depth of said defect, and means to grade the depth of said defect responsive to the selected differential amplifier which provides an output signal, and second means to combine said means to grade the defect with said first means to combine.

10. Apparatus as set forth in claim 8, wherein said defect width grading means comprises means to discretely measure said width to fall within at least two specific width ranges for grading said defect width.

11. Apparatus as set forth in claim 10, wherein said means to discretely measure said width comprises three counters connected to said first pulse forming means, each of said three counters being set to different respective values for grading said defect width.

12. Apparatus as set forth in claim 8, wherein said defect quantity grading means comprises means to discretely measure said quantity to fall within at least two specific quantity ranges for grading said defect quantity.

13. Apparatus as set forth in claim 12, wherein said means to discretely measure said quantity comprises three counters connected to said first counter means, each of said three counters being set to different respective values for grading said defect quantity.

14. Apparatus as set forth in claim 8, wherein said defect length grading means comprises means to discretely measure said length to fall within at least two specific length ranges for grading said defect length.

15. Apparatus as set forth in claim 14, wherein said means to discretely measure said length comprises three counters connected to said second counter means, each of said three counters being set to different respective values for grading said defect length.

* * * * *